United States Patent [19]
Gilmer et al.

[11] 4,014,323
[45] Mar. 29, 1977

[54] ELECTROTHERAPY SYSTEM

[76] Inventors: James Ray Gilmer, 510 Nesbitt Drive, Garland, Tex. 75041; Harry Alvin Bowers, 305 Edgefield, Garland, Tex. 75040; Robert Earl Day, 1502 Hiawatha Drive, Garland, Tex. 75041

[22] Filed: June 30, 1975

[21] Appl. No.: 591,402

[52] U.S. Cl. .............. 128/2.1 Z; 128/409; 128/422

[51] Int. Cl.² .............. A61B 5/05; A61N 1/36

[58] Field of Search ......... 128/2.1 R, 2.1 C, 2.1 Z, 128/303.18, 404, 409, 416–418, 419 R, 420, 421, 422

[56] References Cited
UNITED STATES PATENTS

| | | | |
|---|---|---|---|
| 521,800 | 6/1894 | Leech | 128/409 |
| 561,046 | 5/1896 | Collier | 128/409 |
| 1,480,353 | 1/1924 | Wappler | 128/417 |
| 1,623,552 | 4/1927 | Pollard | 128/409 |
| 1,684,859 | 9/1928 | Catlin | 128/409 |
| 2,864,371 | 12/1958 | Parodi | 128/419 R |
| 3,373,747 | 3/1968 | Tappler | 128/422 |
| 3,490,439 | 1/1970 | Rolston | 128/410 |
| 3,859,983 | 1/1975 | Dohring et al. | 128/2.1 Z |
| 3,866,600 | 2/1975 | Rey | 128/2.1 R |
| 3,894,532 | 7/1975 | Morey | 128/2.1 C |
| 3,900,020 | 8/1975 | Lock | 128/422 |
| 3,908,669 | 9/1975 | Man et al. | 128/422 |

FOREIGN PATENTS OR APPLICATIONS 1,515,840 9/1965 France .............. 128/2.1 C Primary Examiner—Robert W. Michell
Assistant Examiner—Lee S. Cohen
Attorney, Agent, or Firm—Olson, Trexler, Wolters, Bushnell & Fosse, Ltd.

[57] ABSTRACT

A system utilizing a low power level of pulsed alternating current for assisting a patient in producing an improved physiological or psychological condition within his body, wherein one improvement in one embodiment lies in a compact portable pulse train generating unit of "pocket-size," and another improvement of another embodiment lies in the combination of an electrotherapy treating unit with a bio-feedback detecting and displaying unit, wherein the patient may visually observe his improving condition during treatment.

3 Claims, 17 Drawing Figures

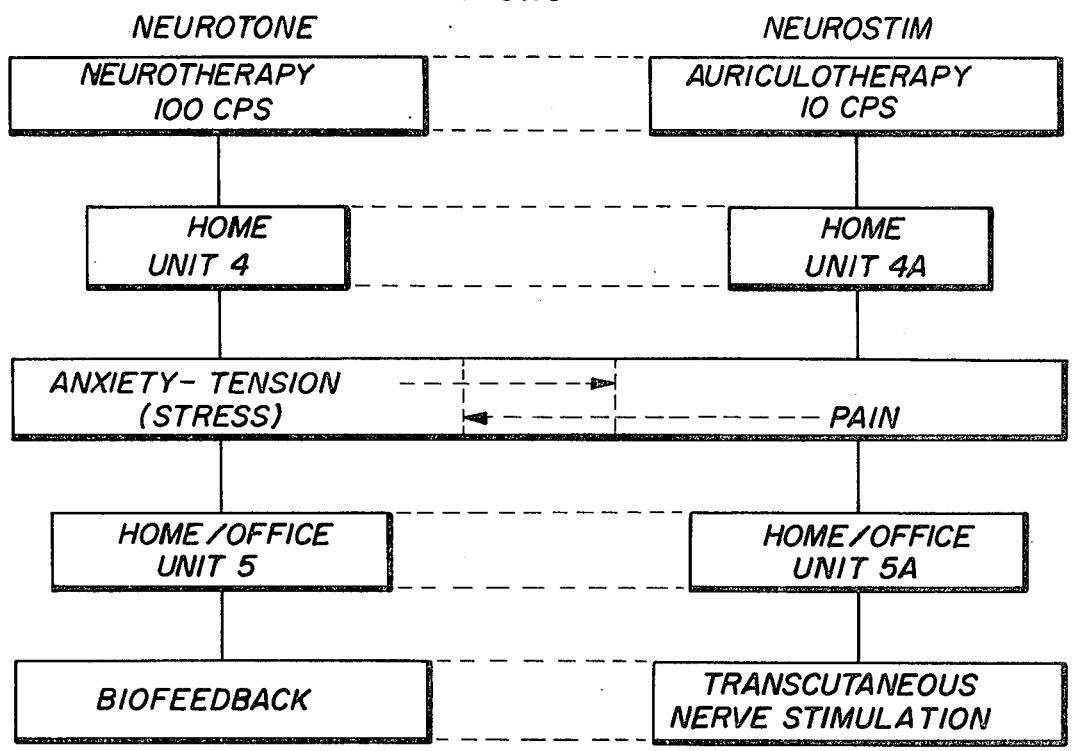
FIG.10
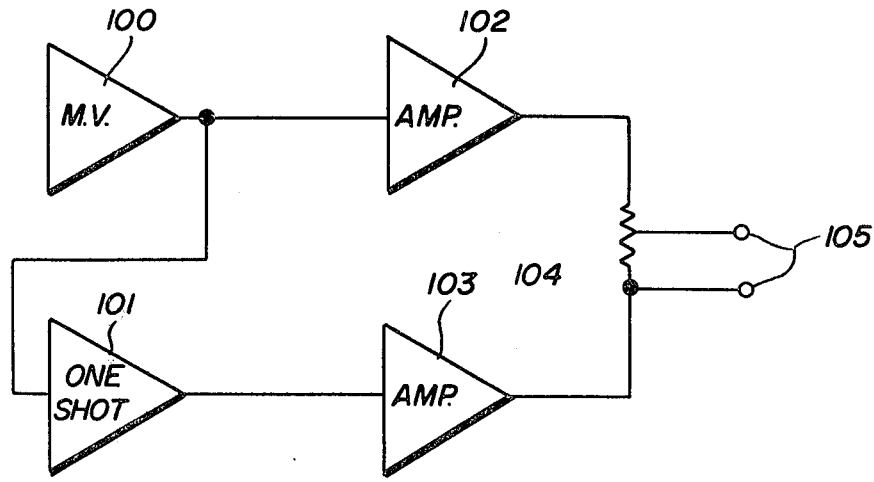
FIG.11
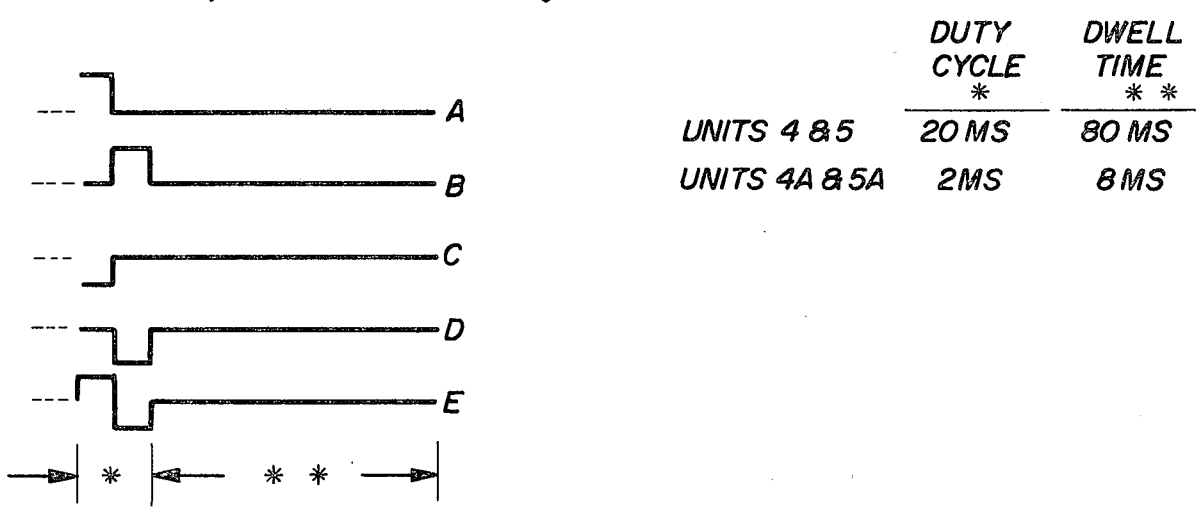

ELECTROTHERAPY SYSTEM

BACKGROUND OF THE INVENTION

1. Field of Invention

This invention relates broadly to the field of systems and machines that employ minute electrical pulses for stimulating or inducing therapeutic actions in persons previously requiring or in need of medication normally employing chemical drugs.

2. Description of the Prior Art

Systems and machines of the general type described herein are in the prior art, the most notable such is probably best seen in U.S. Pat. No. 3,718,132, of William J. Holt and Roger Boy de la Tour, entitled Electrotherapy Machine, which is assigned to the assignee of the present invention.

In systems of the patented type, electrodes for transmitting electrical energy into the body of the patient were generally applied to the forehead by holding straps or a headband. Systems using this manner of attachment have now been improved in the following ways:

a. The unesthetic and objectionable strap or attaching band has been eliminated.

b. The location of the electrodes has been moved from the forehead to area of the ears where their effectiveness is notably improved because the nerve endings are closer to the surface in this area.

c. A simple, easy to use, set of electrodes has been provided.

d. A more economical unit has been provided for renting or selling to a patient for home use.

These advantages have been accomplished by the adaptation and conversion of a standard stethoscope-type set of sound control ear plugs into a treatment application device. The result is that a very attractive and easy to apply head set provides the patient attaching electrodes which may be removed at will and may actually be used in a public or semi-public location where taped or strapped on electrodes would not be practical and would be an embarrassment for the user. By contrast, a person employing strapped on electrodes would immediately be classed as an "out-patient" and would be largely avoided by his peers, whereas a person employing the head set type electrodes would be at first thought to be listening to a radio or recording and would be accepted at any social level. This has been found to be true even after an identification has been made of its use. One, not immediately apparent, reason why this social acceptance is so important, is that one of the abnormal conditions that is effectively treated by electrotherapy (sometimes called cerebral electrotherapy or CET) is "neurosis," and one of the side effects or neurosis is the difficulty of social adjustment. So a patient who would ordinarily be inhibited from using a socially unaccepted machine, has no problem even in receiving treatments in public places wherever the need arises. The combination of a pocket-size unit with a conventional appearing head set poses no psychological problems even with patients having more serious than normal neuroses.

Other objections to the use of the prior art headbands are: that they are suggestive of the very traumatic electric shock treatment and may be shunned for this reason; and the headbands require more skill to adjust and tend to work loose and allow the electrodes contained therein to lose electrical contact with the skin surface when the patient moves his head. A primary factor in favor of the use of ear electrodes is the ease of use afforded a patient in his home environment. Other important favorable factors are that a shorter time and a lower stimulation current are required with the ear electrodes than are required for an equivalent treatment using the prior art electrodes. While prior art CET units were treating patients in physicians' offices, clinics, and hospitals, this use did not meet the full spectrum of treatment needs. An economical, ultra simple, easy to use, easy to carry (in purse or pocket) unit, powered by standard batteries, with an electrode set that would not be so embarrassing or complicated as to discourage home use was needed, and this need is fulfilled with the present invention. And the present invention is especially beneficial to those patients who require prolonged treatments or have difficulty getting to their physician's office and may conduct their own treatment, after proper instruction, in their own home.

Other prior art machines and systems are seen in the references cited in the above mentioned patent, and in the references cited in Donald D. Maurer U.S. Pat. No. 3,817,254. However, while the prior art disclosures serve useful functions in their respective fields, none of them accomplish the Applicants' purpose in the manner or with the structure of the present invention as described herein.

The disclosures of U.S. Pat. Nos. 3,178,132 and 3,817,254 and the references therein are incorporated herein by reference and form a part of this disclosure.

SUMMARY OF THE INVENTION

A principal object of this invention is to provide a simple, straight-forward, easy to use, and fool-proof electrotherapy unit that will be both safe and effective for home or office use by a patient under the direction of his physician.

Another object is to provide a method of treatment that is effective for a wide range of human disorders, principally in the stress and neurosis areas, but effective in other areas as well, that may be self-administered both at home or in public places when needed.

A further object is to provide an electrotherapy treatment unit which is conveniently portable and wherein the electrical circuitry and power supply are miniaturized to a compact size (to fit conveniently in a lady's purse or a man's shirt pocket) and wherein the applicator portion including the electrodes is easily disconnected from the main unit and it also is transportable in a pocket size.

An additional object is to provide an applicator portion for a CET unit that is removable from and interchangeable with electrotherapy treatment generating units of different sizes and complexities so that an individual's head set applicator, which is considered personal for hygenic purposes, may be used selectively with a large varied function doctor's office console unit, or with a smaller table-top home unit or with a completely portable unit.

And yet another object of this invention is to provide an applicator portion for a patient treatment CET system that employs a standard heat set frame that has a familiar appeal to a patient, but which includes subtle modifications necessary to render it effective for the purpose intended.

Other objects of the present invention are to provide an electrotherapy unit which includes both audio and visual bio-feedback, means to simultaneously treat and measure the functioning of the unit and the effectiveness of the treatment.

BRIEF DESCRIPTION OF THE DRAWINGS

FIG. 10 is a block chart showing the usage range of the various embodiment systems of this invention.

FIG. 11 is a functional diagram of the stimulator circuit of the units described herein.

DESCRIPTION OF PREFERRED EMBODIMENTS

Figure 2:
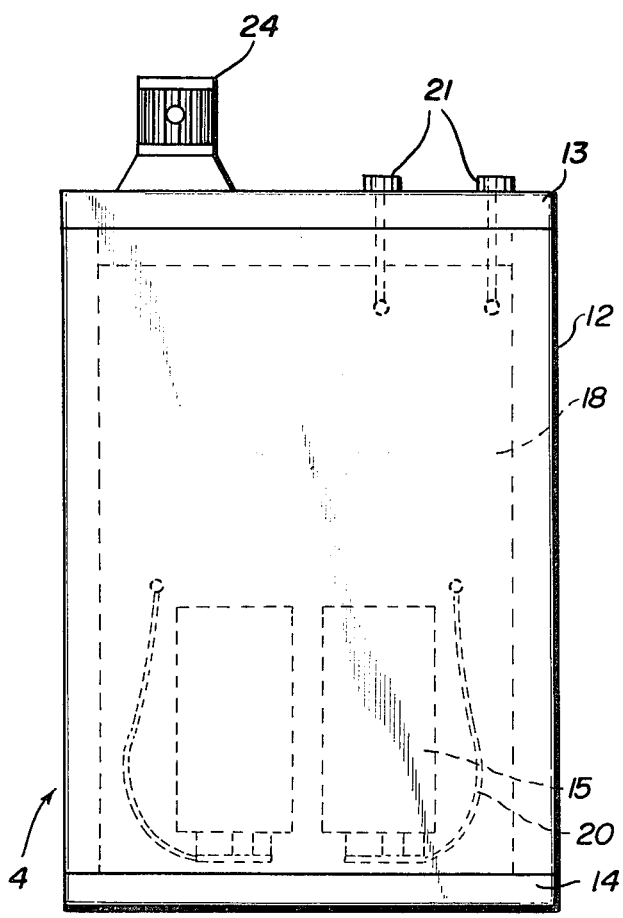
FIG. 2 is an enlarged detailed elevational view, partly in schematic arrangement, of the fully portable CET pulse train generating unit shown in FIG. 1.

The generating unit shown in FIG. 2, including its accompanying head set electrodes, is intended to be sold by a doctor's prescription only and will be designated hereafter as the "prescription unit." This unit is fully portable and may be taken home by a patient and used by him after a physician's direction. For this purpose the unit is simple to operate, small in size (fits easily in a person's purse, or pocket), rugged in construction so that it is virtually impossible to damage in ordinary use, sealed so as to prevent moisture or detrimental particles from becoming lodged in the internal circuitry where either might interfere with the proper functioning, certified so that malfunction is not possible under normal operation conditions, extremely safe since the maximum electric current possible is in the milliampere range (example 0.8 m.a.) from batteries of the small transistor radio size with no possibility of usage with house current, stethoscope type ear electrodes permit immediate detection and removal of uncomfortable electric voltage level together with immediate resetting of a simple signal dial on the pocket-size generating unit.

Figure 5:
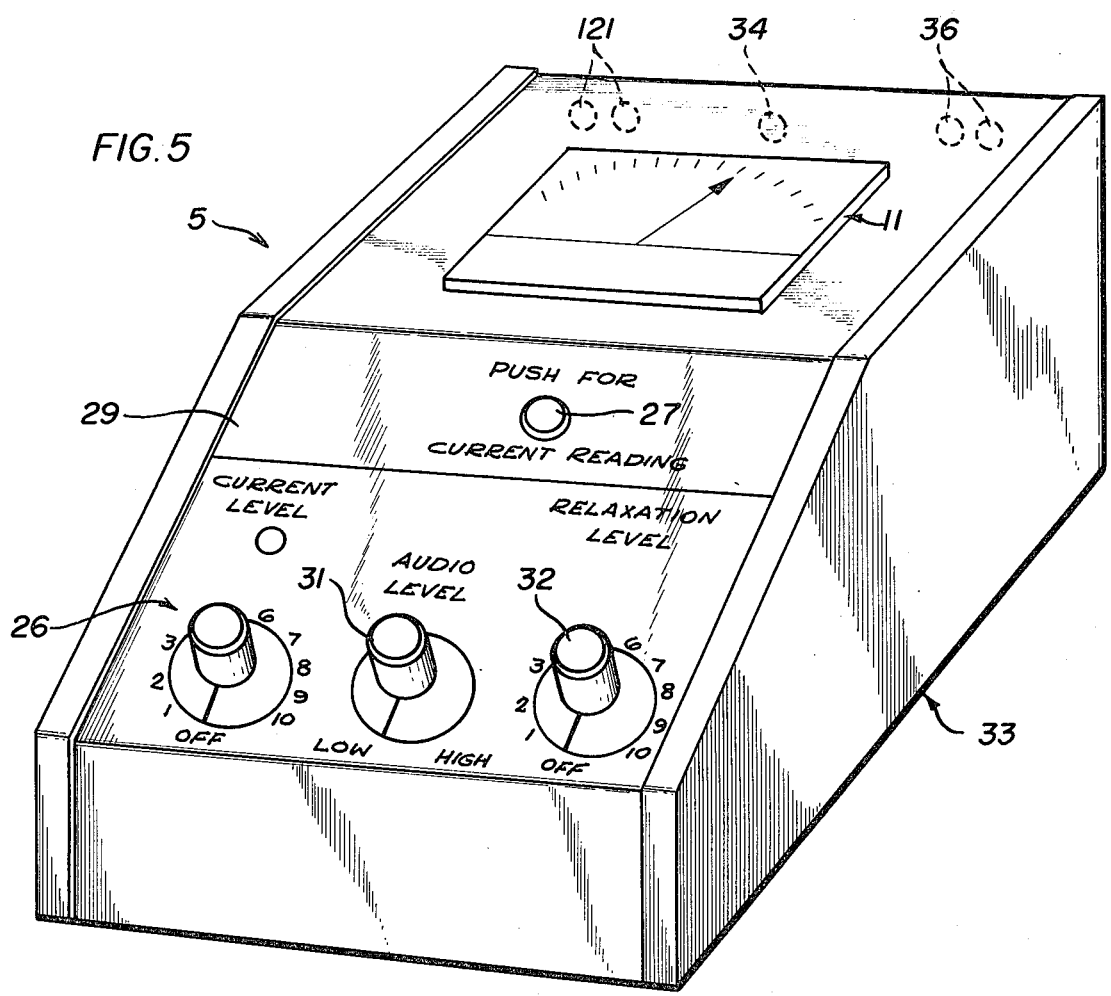
FIG. 5 is a perspective view of the table-top CET generating unit shown in FIG. 1.

The generating unit shown in FIG. 5, including its accompanying head set and finger-tip electrodes, is intended to be sold for use either in a doctor's office and/or for home use in special circumstances and will be referred to hereafter as the "office unit." This unit is designed to be placed on a desk or table top when in use, and while it is light enough in weight to be manually carried about, it is not normally classified as highly portable (i.e., as purse or pocket size). But rather the unit is designed to be used by a patient in the doctor's presence while both are seated, or at home by a seated or reclining patient. The unit has a slant front for easy reading of the instrument dials and its case has a walnut or other finish that is compatible with contemporary decor normally associated with a doctor's office. This unit is made to meet all of the requirements of the home "prescription unit," except of course that unit's high degree of portability. The "office unit" also possesses many additional features not present in the "prescription unit" that will be described more fully hereafter.

The basic electronic circuitry disclosed in the Holt, et al, patent may be used with this invention, so the disclosure herein will concentrate on the structural improvements that facilitate the continued usefulness of the patented circuitry in providing advancements to meet the enlarging needs in the field of electrotherapy as this relatively new science emerges and becomes more widely acknowledged and accepted. Certain, herein disclosed, electronic modifications and improvements, not shown in the prior patents, will be seen to supplement the state of the art where applicable. The prior art circuitry will be shown as block diagrams herein.

It is known and reported that the human body (including its mental facilities) is in a healthy state when all of its activities, including microbioelectric impulses, are functioning normally. The system of the present invention produces microelectronic impulses that provide a normalizing assist to the usually naturally self-regulating and self-correcting functions, which when normal, satisfactorily occur within the body's own network of bioelectric signalling and control until excessive environmental chemicals, bacteria or emotional stresses disrupt these functions bringing states of illness or deviations from the normal functional patterns of good health. Such normalizing assists are believed to be both corrective and preventive in character. It becomes preventive when the normalizing assist replaces abnormal stereotyped physical or mental response patterns with normal patterns resulting in greater resistance to any description of normal functional patterns of good health.

Figure 1:
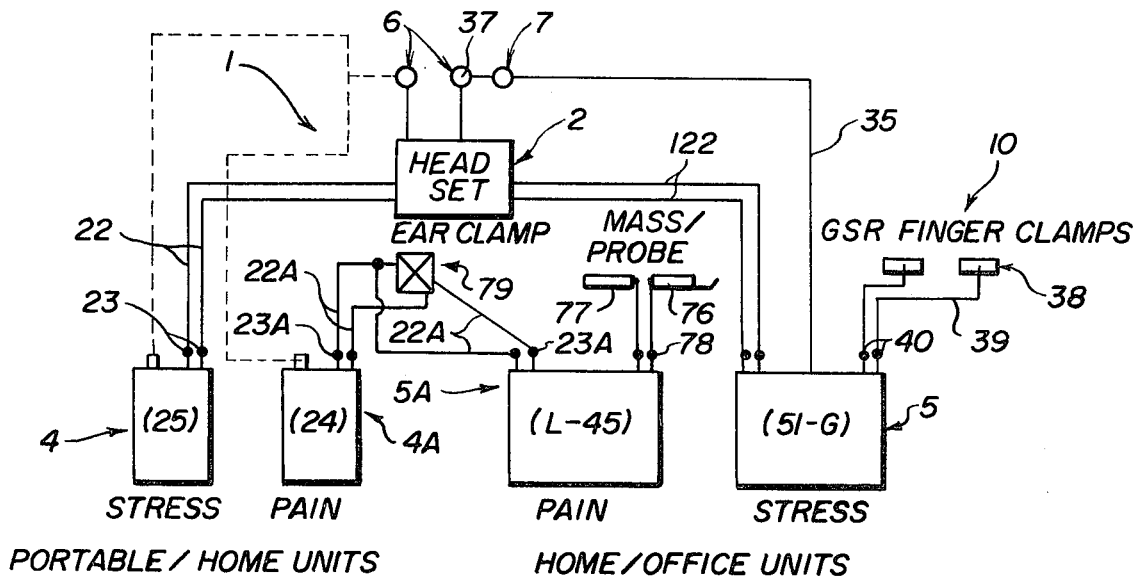
FIG. 1 is a block diagram showing the total system and the individual units selectively making up this system in an interchangeable manner.

Referring now more particularly to the characters of reference in the drawing it will be seen in FIG. 1 that the overall system 1 of this invention has a common focal point in the form of the head set unit 2, which utilizes the output (though usually not simultaneously) of each of the instrument units 4, 4A, 5 and 5A. The "stethoscope type" head set electrodes 6 are usable with the prescription ("ultra" portable/home) units 4, 4A (FIGS. 2–4) and the home/office units 5, 5A (FIGS. 5 & 12) (which are also highly portable, but to a lesser extent than units 4, 4A). The head set 2 may also include an audio unit 7 for measurement and test purposes when used with unit 5.

Unit 5 also incorporates, in addition to an active stimulator, a passive system whose primary purpose is not to achieve therapy by means of active stimulation, but to provide a general indication of a subject's emotional stress state and an indication of change in that emotional stress state. The means by which this is accomplished is to measure the galvanic skin (electrical)

resistance by applying usually less than 50 micro amperes of galvanic (D.C.) current to two electrodes usually on the tips of first and third fingers on the right hand, amplifying this and showing the changes in resistance by a sensitive meter. This is usually a passive system because the purpose of applying any current to the subject is for the purpose of providing a means of showing active changes which the subject (not the device) is "generating" which is known to represent changes in the subject's emotional response to environmental events or thoughts about environmental events.

Headband electrodes 8 (FIG. 8A) were used with prior art heavy duty office units (not shown) but not with units 4–5A. Two of the reasons being that head set 2 is easier to use and more appealing than the headband 9 required with electrodes 8 and the usually higher current drain of electrodes 8 shortened battery life to a less acceptable period than with head set 2.

Figure 6:
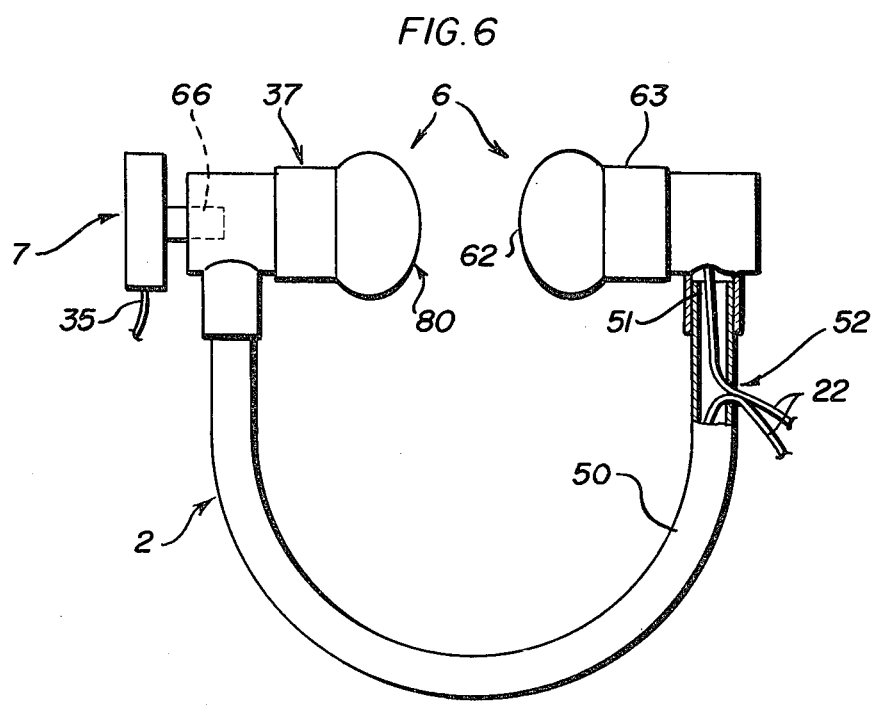
FIG. 6 is a detail view of the head set applicator unit that is interchangeably used with the generating units of FIGS. 2–6.

The audio unit 7 of FIGS. 1 and 6 is used with a single terminal 37 of electrode unit 6 of the stethoscope head set 2, but there is no provision to use it with headband electrodes 8 or any of the prior art units, which is another distinct advantage of the head set unit 2. The principal use of the audio unit 7 is for bio-feedback measurement purposes which are of interest to both the physician and the patient, as are all of bio-feedback measurements herein contained. For example, a patient can observe his own stress reactions by noting the change in frequency of the sound clicks of the audio unit 7, or by visually observing the change in movement of the indicator needle of the milliampere gauge 11 of instrument unit 5 whenever his reactions to environmental stimuli change and are transmitted to the unit 5 through the GSR (galvanic skin reflex) unit 10. This observation by the physician and the patient will help the patient understand what is causing the stress, and more importantly, will help the patient to watch for and be prepared to change his attitude (and hence his reaction) to these causes. This bio-feedback will help the patient recognize how environmental factors affect his emotional stress state, how active CET treatment can bring a reduction in the emotion stress state and provide a measurement of progress as the patient works to retrain himself to better more healthy responses to environmental stimuli.

Figure 3:
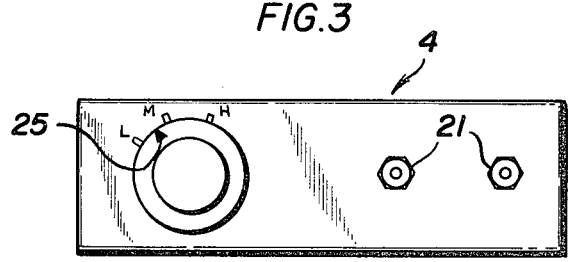
FIG. 3 is a top plan view of the device of FIG. 2.
Figure 4:
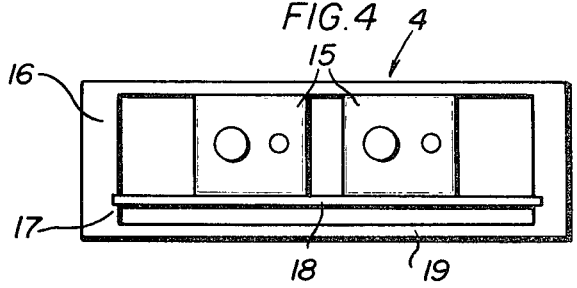
FIG. 4 is a bottom view of device of FIGS. 2 and 3 with the bottom cover removed.

FIGS. 2–4 show the prescription unit 4 to consist of a rectangular housing (approximately 4 × 2.5 × 1 inches in dimensions) that will conveniently fit in a person's purse or shirt pocket. FIG. 2 shows the generating works to be housed in an insulating material case 12 having a top plastic insert 13 and a bottom plastic insert 14 that is readily removable to permit replacement of transistor radio type batteries 15. The interior of case 12 is basically hollow and rectangular in cross section as shown in FIG. 4. At corresponding locations on side walls 16 a groove 17 has been formed to receive a printed circuit board (PCB) 18 which is inserted and retained in parallel disposition to elongated side walls 19. PCB 18 contains the electronic circuitry shown in FIG. 11 and forms the generating works of unit 4. Batteries 15 deliver direct current power to PCB 18 through leads 20 and the short duration pulses of alternating current whose vectorial sum is zero appears at the output terminals 21 for transmittal to the head set electrodes 6 through leads 22 via jack plugs 23. Knob 24 on top plate 13 is rotated to change the amount of current of the electric power output coming through terminals 21 and hence to head set electrodes 6. FIG. 3 shows three marked settings of the arrow 25 of control knob 24, which settings may be identified as $l$, $m$, $h$, for low, medium and high, and represent a clockwise rotational advance of knob 24. The unit 2, as disclosed, may be operated from a hand held or lap held position, or may be operated while still contained in a purse or pocket by merely rotating knob 24 until the proper comfort level of electric power intensity is reached. There are no other controls or adjustments required, and there is no possibility of a dangerous electrical power level being reached, since the maximum output of the two 9 volt batteries at the high knob setting is less than 1 milliampere.

The generating unit embodiment shown in FIG. 5 is identified as the "home/office unit" 5 and employs basically the same generating works as unit 4 as far as the stimulation portion goes, i.e. control knob 26 performs the same basic function as control knob 24, except it contains ten marked positions instead of three. Unit 5 additionally includes an audio unit 7 and a GSR unit 10, and a milliampmeter 11 and a push button 27 for selective reading of the current level determined by the setting of control knob 26. Looking at the inclined instrument control panel 29 it is seen that in addition to the stimulation current level control knob 26, there are also included control knob 31 for audio level adjustment and control knob 32 for relaxation level adjustment. On the back side of housing 33 of unit 5 are located the color coded plug-in output terminals 121 for the stimulation circuitry output, terminal 34 for the audio generating circuitry output, and input terminals 36 from the GSR bio-feedback unit.

As a patient is receiving electrotherapy stimulation treatment, as for example through leads 122 from unit 5 via terminals 121 and head set 2, he may also be "plugged in" to receive audio signals from terminal 34 through lead 35 and transmitter 7 which is directly plugged into one ear pad terminal 37 (see FIGS. 1 and 10), and to transmit GSR bio-feedback information from unit 10 attached to his person through finger units 38 and leads 39 to input terminals 36 via jack plugs 40 (FIG. 1). When so equipped, the patient can monitor his response both before, during and after therapy treatment.

Figure 7:
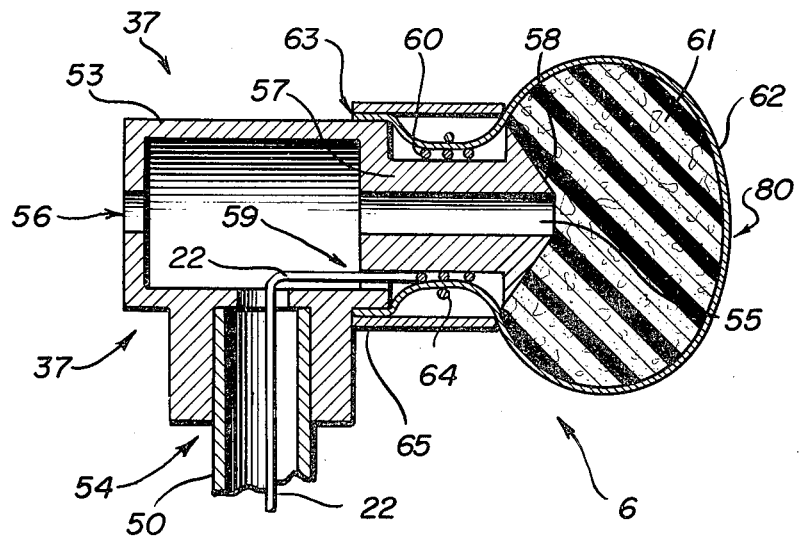
FIG. 7 is an enlarged detail cut-away view of one of the electrodes of the device of FIG. 10.

Referring now to FIGS. 6 and 7, the novel applicator of this invention may be observed. The head set unit, identified as 2, is comprised of a U-shaped tubular frame 50 having two open ends 51 and a single side wall opening 52 and wherein each open end engages an ear terminal unit 37. Lead wires 22 terminate at their distal end in plug-in jacks 23 for engagement with terminals 21 of prescription unit 4, 4A or with terminals 121 of home/office unit 5.

The ear terminal 37 is seen in FIG. 7 to comprise a hollow cap 53, open at its lower end 54 and opposite sides 55 and 56. End 55 includes a necked down portion 57 terminating in an enlarged tip 58. One lead wire 22 goes to each ear terminal and is secured to cap 53 by passing through opening 59 and thereafter being wrapped several times around neck 57 to form a loop terminal 60. A small sponge type cushion 61 of foam plastic or similar material contacts the tip 58, and this cushion is held in place by silver coated nylon loops of Velcro cover 62 in the shape of a bag whose open end 63 is squeezed into continuous contact with the loop terminal 60 and held there by a single ring of a relatively heavy wire 64 which acts as a closing spring. This area is then covered by a short section of shrink tubing 65. The area of the lead 22 in the area of neck 57 is bare for electrical contact with the silver coated Velcro loop (or bag) which is itself a good conductor of the small electric currents which must then make contact with a portion of the patient's body (usually in the vicinity of the ear) for transcutaneous conduction to the other terminal 37 located elsewhere on the patient's body. Since the loop 62 is porous, as is the cushion 61, ordinary tap water may be absorbed by the cushion to conduct electrical current between the lead wire terminal 60 and the patient's skin which terminals 37 engage. The engagement between the tubular member of downwardly opening end 54 and the upper open end of tubular structure 50 is such that terminal 37 may be rotated with a moderate pressure to provide an optimum engagement position with the patient. One or both of the ear terminals 37 may have an opening (56), to receive the engagement plug 66 of audio unit 7. The audio signals are easily transmitted from unit 7 through plug 66, through the hollow chamber of shell 53, and through opening 55, cushion 61 and cover 62 to the patient's ear drum and also through hollow tube frame 50 around to the other ear.

Figure 8A:
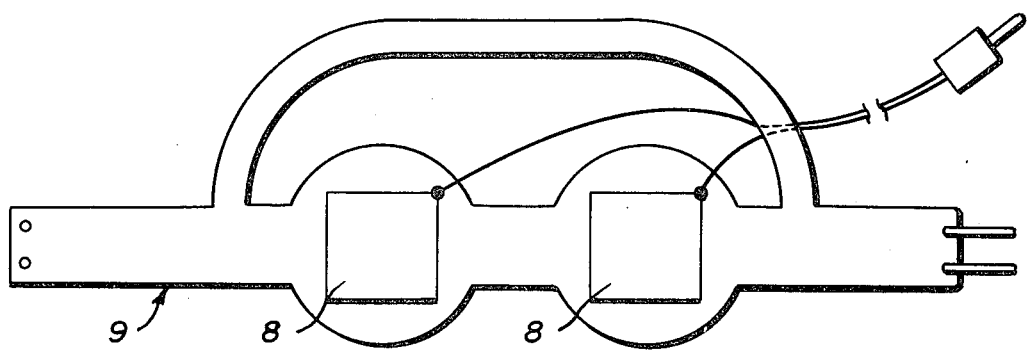
FIGS. 8A and 8B are plan view showing prior art applicator units used with CET generating units.

FIG. 8A shows the prior art headband 9 which have been previously described. Another objection to the use of such headbands by patient and family is that they are similar to the electrode placement apparatus used for the sometimes terrifying electroshock therapy. Such an image might imply a more serious condition than the patient is actually experiencing. No such stigma (justified or not) attaches to the use of the familiar stereo type head set electrodes of the present invention as a similar head set is regularly used by secretaries transcribing dictation and by jet plane travelers listening to high fidelity music in flight.

Figure 8B:
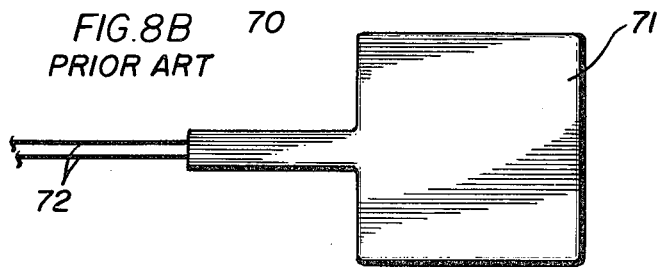
Figure 9:
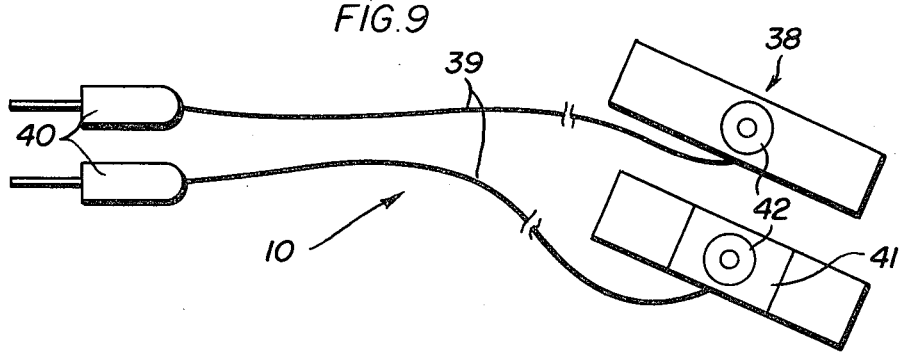
FIG. 9 is a plain view of the finger electrode set used for bio-feedback purposes with one embodiment of this invention.

FIGS. 8A and 8B are both local body surface stimulation electrodes of the prior art which are attached to the subject's body, usually at acupuncture or electroreceptor points or at the point of pain by adhering or adhesive tape, for the purpose of relieving existing pain. While electrodes of FIG. 9 are generally used only passively to measure GSR reactions of a patient, we have found they may be employed beneficially for both pain and stress relief. When so employed an extra amount of Spectra-gel 360, which is a conductive jelly employed to make better electrical contact between the electrode and the subject, is usually employed.

Any of these electrodes may be located at points referred to by Western Hemisphere medical practice as trigger points, which may or may not coincide with acupuncture points.

The unit 70 of FIG. 8B includes a paddle shaped non-porous conductive rubber electrode 71 affixed to the end of a lead wire 72. This unit is taped to the skin of a patient, and while effective for its primary purpose, it has some side effects that are eliminated by the present invention. For example, the taping on and removal of the tape is a time consuming, irritating and sometimes painful experience, and the prior art rubber electrodes seal off the air and do not "breathe" (as does the foam cushion and nylon cover of the applicants' units of FIGS. 6, 7, 13A and 13B) which difference may cause a rash under the solid rubber electrode and tape of the prior art unit. Also, obviously, neither of the prior art electrodes are adapted to engage to concha area of a patient's ear, which has been found very effective for electrotheraphy due to the close proximity of the nerve endings to this area. Applicant's electrodes 85 of FIG. 13B consist of folded pads 85A of Velcro with a metal contact of the side away from skin contact. These electrodes are similar to electrodes 41 of GSR finger units 38 that are coplamar with metal terminals 42. The folded pads 85A avoid direct contact of metal with flesh.

FIG. 10 is a chart that shows diagrammatically the basic benefits of the CET systems of the present invention and the general areas of effectiveness of treatment available therewith. Under the "Neurotherapy" heading, problems associated with "Anxiety" and "Tension" are classified, while under "Auriculotherapy" the problems associated with "Pain" are classified. In these two general heading categories, a simple home unit and a more sophisticated office unit are recommended as uniquely effective, but with an area of overlapping mutual effectiveness. A word of explanation of the well-known (in medical circles) concepts of "neurotherapy," "auriculotherapy," etc., used in FIG. 10 may be in order. "Therapy," of course, is recognized as "treatment," and "neurotherapy" is a specialized treatment applied to some part of the nervous system, primarily to relieve anxiety and tension. Auriculotherapy is a specialized treatment primary to relieve pain that is applied to a particular area of the outer ear because it has been found that nerve endings occur near the surface of the skin in the outer ear in a precise relationship to the origin of pain to those nerves in other areas of the body (see published manual by Paul F. M. Nogier, M.D., with the title: "Treatise of Auriculotherapy" printed in France in 1972 (language is English), which publication is incorporated herein by reference.

As noted in U.S. Pat. No. 3,718,132, of the same Assignee as the present invention, the electronic circuitry of these inventions utilizes a low power direct current (from batteries) as the input source, and converts this power to trains of alternating pulses whose vectorial sum is zero. In the present invention this basic circuitry has been miniaturized in units 4 and 4A to provide an ultra portable home unit that operates from an input of two 9 volt D.C. transistor type batteries to provide an output of alternating current pulses with a frequency of 10 to 100 cycles per second and a 20% duty cycle all contained in a package of less than 4 × 2.5 × 1 inches in size. Home unit 4 (100 cps) is primarily suited for treatment of "stress," whereas a companion unit 4A, whose output frequency is only 10 cps. is more suited for relief of pain. The corresponding home/office units would be 5 and 5A as seen in the chart of FIG. 10 and their output frequencies correspond to their home unit counterparts, except that unit 5A is adjustable to both frequencies.

FIG. 11 shows a functional block diagram utilized by all of the embodiments of the present invention. In operation of units 4 and 5 the multivibrator 100 generates a positive pulse shown at A of 10 ms. duration and then remains off for 90 ms. with the application frequency within each pulse of 100 cps. The negative edge of the pulse triggers a "one-shot" 101 into giving a positive output of 10 ms. duration and it also then remains off until re-keyed by another negative edge. The positive pulse (at A) is inverted and amplified (at C) when passing through inverting power amplifier 102. The positive pulse (at B) is inverted and amplified (at D) when passing through inverting power amplified 103. The resulting voltage (at E) across the output (105) appears as an alternating current voltage of approximately twice the input voltage for a 20 ms. duration and an off or dwell time duration of 80 ms. In operation of units 4A and 5A, which are specific for pain relief, the duty cycle is 2 ms. duration and the off time duration is 8 ms. with an application frequency within each pulse of 10 cps.

Figure 12:
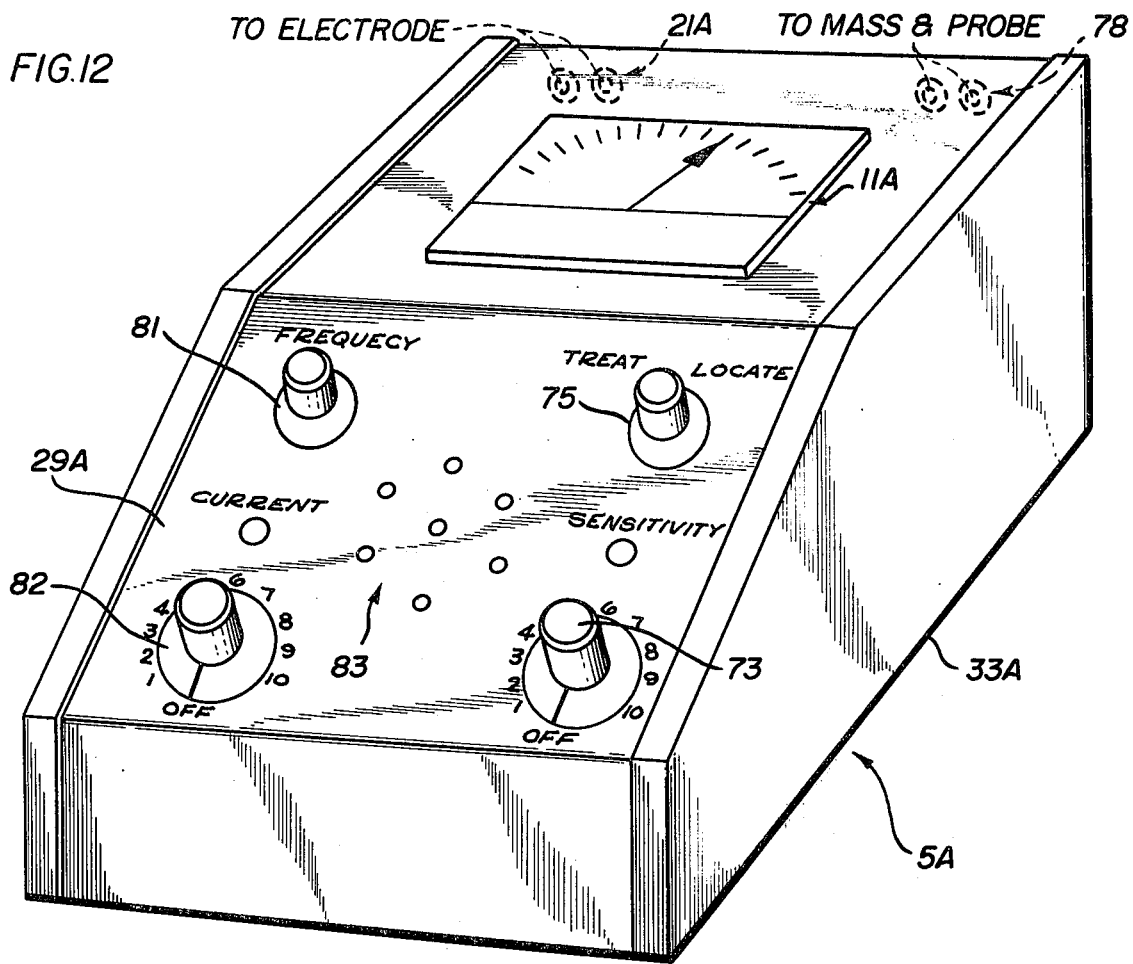
FIG. 12 is a perspective view of a home/office table-top mounted pain relief console unit.

FIG. 12 is a perspective view of home/office unit 5A which is primarily intended for use in relieving pain but is equally useful in stress relief. This unit includes a milliameter 11A that corresponds to that shown in FIG. 5. This unit 5A is functionally separated into two systems, one for locating and one for treating pain, and the desired system is selected through knob 75 on the inclined front panel 29A of console 33A. With the knob 75 set in the "locate" position, probe 76 and mass 77 (shown in FIG. 13C) are inserted into jack terminals 78 on the back panel of unit 5A. A patient holds the mass 77 in one hand and after setting the sensitivity control 73 to the desired voltage, the physician runs the probe 76 along the patient's ear until a marked increase in current registers on milliameter 11A. This increased current signifies that the probe has hit a surface area of lowered resistance which identifies the location of the nerve endings corresponding to the area of pain/disorder elsewhere in the patient's body. It is known from auriculotherapy that substantially all the body surface is represented at specific areas on the external ear.

Once the very low continuous current probe action is completed, an ear clamp 79 employing a higher (but still in the millampere range) current is clamped in the located pain location for pain relief purposes. The ear clamp 79 includes electrode pads 80A which are constructed in the same manner as pads 80 of head set 2, and leads 22A which terminate in jacks 23A which plug into terminals 21A on the back panel of unit 5A (similarly in unit 4A). For pain relief the frequency knob 81 is set to the 10 cps. frequency and spaced pulses of electric energy enter the patient's ear through the ear clamp electrode pads 80A. The intensity but not the frequency of these pulses is varied through current selector knob 82.

The current from probe 76 that causes milliameter 11A to change its reading may also be directed through an audio signal unit (whose output location is at 83) to give an audible reading of the current changes.

Figure 13A:
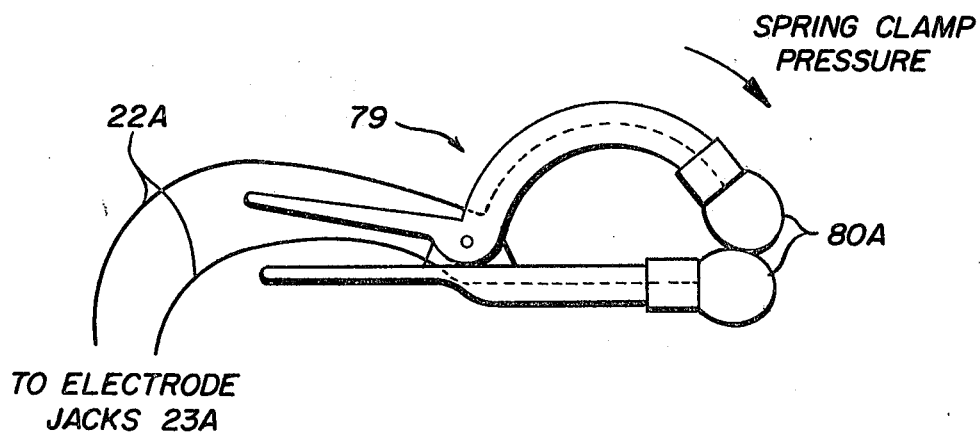
FIG. 13A is an ear clamp electrode used with the console unit of FIG. 12.

FIG. 13A shows the details of construction of the ear clamp 79. It will be noted that the pad electrodes 80A are similar to pads 80 shown in FIG. 7. Other construction details likewise correspond to those shown in FIGS. 6 and 7.

Figure 13B:
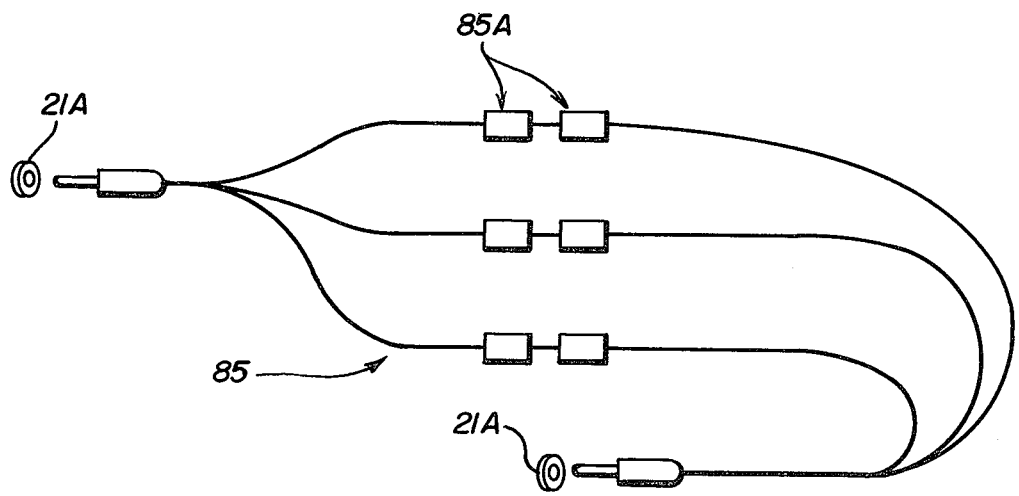
FIG. 13B is a pad loop electrode used with the console unit of FIG. 12.

FIG. 13B shows that electrode set 85 may be plugged into terminals 21A for applying the output of unit 5A directly to areas of pain on the body surface. The electrodes 85 may be taped onto the body with "Dermicel" porous adhesive tape so that both the tape and the Velcro porous electrode pads may "breathe" and reduce skin irriation.

Figure 13C:
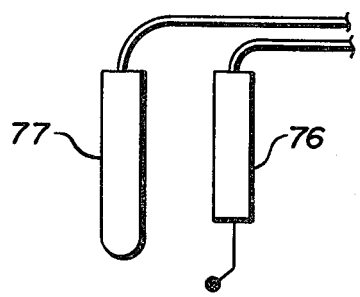
FIG. 13C is a prior art mass and probe set used with the console unit of FIG. 12 for locating specific pain areas.

FIG. 13C shows the mass 77 that may be held in the patient's hand while the physician uses the probe 76 to locate specific pain areas on the body, or to locate their counterpart area on the outer ear. Once the pain area is located by probe 76 it may be treated with the same instrument 5A.

Figure 14:
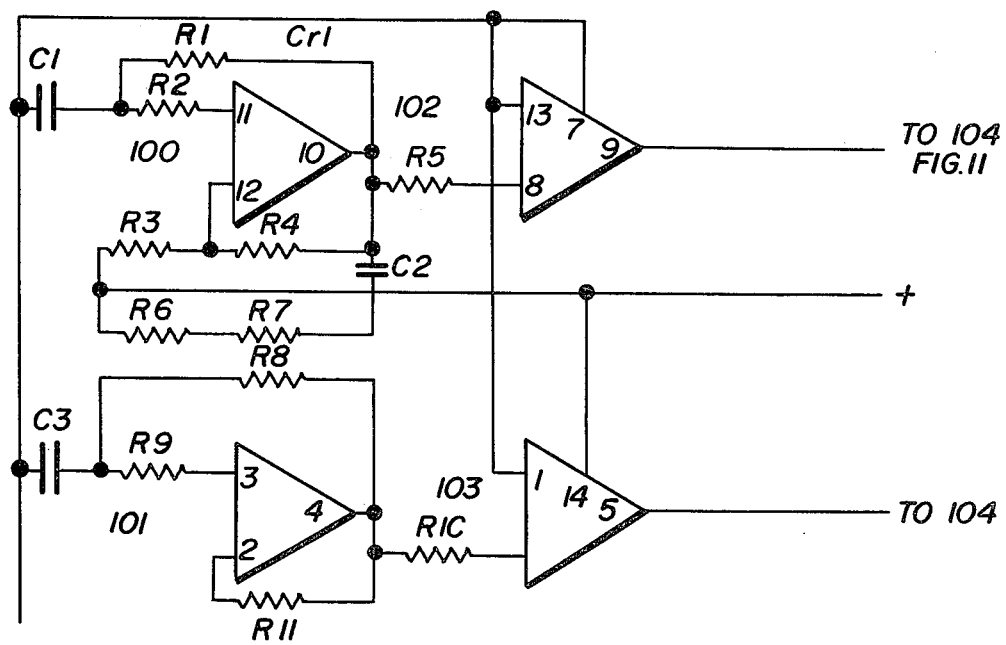
FIG. 14 is a detail circuit diagram of the "stress" stimulator circuitry of this invention.

FIG. 14 is a detailed circuit diagram of the "stress" stimulator circuitry (shown in FIG. 11) of the pulse generating units described herein. Since the therapy for stress involves stimulative pulses having 100 cps frequency, capacitors C1 and C3 are of a set value and are installed in the circuit in a fixed manner. When this circuit is employed for "pain" therapy, the frequency required is 10 cps, and capacitors C1 & C3 are not installed directly in the circuit shown, but rather through the 100 cps position of frequency selector switch 81 (FIG. 12). The other position of switch 81 cuts into the circuit other capacitors having the necessary value to provide a frequency of 10 cps.

The invention is not to be limited to or by details of construction of the particular embodiment thereof illustrated by the drawing, as various other forms of the device will, of course, be apparent to those skilled in the art without departing from the spirit of the invention or the scope of the claims.

We claim:

1. An electrotherapy system comprising: pulse train generating means for providing a series of bursts of low level electrical energy, including output terminal means; patient-engaging means, including input terminal means connectable in electrical circuit with said output terminal means and further including electrodes in circuit with said input terminal means for transmitting said bursts of electrical energy to a patient needing therapeutic treatment; control means for manually adjusting the relative level of electrical energy produced by said pulse train generating means; and passive, measuring means for indicating the patient's emotional stress state and changes therein, simultaneously with treatment using said bursts of energy, including galvanic skin electrical resistance sensing means.

2. An electrotherapy system according to claim 1 wherein said measuring means includes meter means for providing a visual indication of said stress state.

3. An electrotherapy system according to claim 1 wherein said measuring means includes sound-producing means for providing an audio indication of said stress state.

* * * * *

UNITED STATES PATENT AND TRADEMARK OFFICE
CERTIFICATE OF CORRECTION

PATENT NO. : 4,014,323
DATED : March 29, 1977
INVENTOR(S) : James Ray Gilmer, Harry Alvin Bowers, and Robert Earl Day It is certified that error appears in the above-identified patent and that said Letters Patent are hereby corrected as shown below:

Col. 2, line 28, "3,178,132" should be --3,718,132--;
Col. 2, line 62, "heat" should be --head--;
Col. 3, line 21, "view" should be --views--;
Col. 3, line 63, "signal" should be --single--
Col. 6, lines 55-56, after "opposite" insert --open--;
Col. 7, line 61, after "nylon" insert --knit--

Signed and Sealed this fifth Day of July 1977

[SEAL]

Attest:

RUTH C. MASON
Attesting Officer

C. MARSHALL DANN
Commissioner of Patents and Trademarks